United States Patent [19]

Stephens

[11] Patent Number: 5,679,832

[45] Date of Patent: Oct. 21, 1997

[54] METHOD FOR MAKING α,β-UNSATURATED-β-TRIFLUOROMETHYL-CARBOXYLATES AND RELATED COMPOUNDS

[75] Inventor: Randall Wayne Stephens, Perkasie, Pa.

[73] Assignee: Rohm and Haas Company, Philadelphia, Pa.

[21] Appl. No.: 727,866

[22] Filed: Oct. 8, 1996

Related U.S. Application Data

[60] Provisional application No. 60/005,004, Oct. 10, 1995.

[51] Int. Cl.$^6$ .................................................. C07K 67/30
[52] U.S. Cl. ............................................................. 560/212
[58] Field of Search ................................................ 560/212

[56] References Cited

U.S. PATENT DOCUMENTS

| 4,464,539 | 8/1984 | Hasimoto et al. | 560/212 |
| 5,075,493 | 12/1991 | Shima et al. | 560/212 |

FOREIGN PATENT DOCUMENTS

| 04282346A | 3/1991 | Japan . | |

OTHER PUBLICATIONS

Walborsky, H. M.; Schwarz, M. J., *J. Amer. Chem. Soc.*, 1953, 75, 3241.
Gassen, K.; Kirmse, W., *Chem. Ber.*, 1986, 119, 2233.
Ishikawa, N.; Koh, M. G.; Kitazume, T.; Choi, S. K., *J. Fluor. Chem.*, 1984, 24, 419.
Bevilacqua, P. F.; Keith, D. D.; Roberts, J. L., *J. Org. Chem.*, 1984, 49, 1430.
Shen, Y.; Wang, T., *J. Chem. Res., Synop.*, 1993, 11, 490.
Ding, W.; Cao, W.; Xu, Z.; Yao, Y.; Shi, Z.; Han, Z., *J. Chem. Soc., Perkin Trans.*, 1993, 7, 855.
Eguchi, T.; Aoyama, T.; Kakinuma, K., *Tetrahedron Lett.*, 1992, 33, 5545.
Iwata, S.; Ishiguro, Y.; Utsugi, M.; Mitsuhashi, K.; Tanaka, K., *Bull. Chem. Soc. Jpn.*, 1993, 66, 2432.
Cook, D. J.; Pierce O. R.; McBee, E. T., *J. Amer. Chem. Soc.*, 1954, 76, 83.
Chen, T. Y.; Gambaryan, N. P.; Knunyants, I. L., *Doklady Akad. Nauk S.S.S.R.*, 1960, 133, 1113, Chemical Abstracts 54:24385g.
Mar., J., in "Advanced Organic Chemistry," 3rd ed., pp. 220–222, John Wiley & Sons, Inc., New York, 1985.
Burger, K.; Helmreich, B., *J. Prakt. Chem./Chem.-Ztg.*, 1992, 334, 219.
Muller, N., *J. Org. Chem.*, 1986, 51, 263.
Ogoshi, H.; Mizushima, H.; Toi, H. and Acyama, Y., *J. Org. Chem.*, 1986, 51, 2366.
Grillot, G. F.; Aftergut, S; Marmor, S. and Carrock, F., *J. Org. Chem.*, 1958, 23, 386.

*Primary Examiner*—Samuel Barts
*Attorney, Agent, or Firm*—Thomas D. Rogerson

[57] ABSTRACT

Disclosed are one and two step methods for preparing α,β-unsaturated-β-trifluoromethyl carboxylates and related materials under mild reaction conditions.

17 Claims, No Drawings ns
METHOD FOR MAKING α,β-UNSATURATED-β-TRIFLUOROMETHYL-CARBOXYLATES AND RELATED COMPOUNDS

This is a nonprovisional application of prior pending provisional application Ser. No. 60/005,004, filed Oct. 10, 1995.

BACKGROUND OF THE INVENTION

The present invention is directed to a method for making α,β-unsaturated-β-trifluoromethyl carboxylates and related materials. Such compounds are useful chemical intermediates, particularly in the synthesis of a variety of useful biologically active compounds such as in the agricultural and pharmaceutical industries.

Methods for preparing α,β-unsaturated esters of Formula I are known.

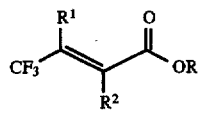

Unfortunately, because of the influence of the trifluoromethyl group, these methods generally require harsh reaction conditions or utilize exotic and expensive reagents to create the double bond. The use of harsh conditions often results in low yields of the desired product, complex mixtures of the product and impurities, and difficult procedures. Exotic and expensive reagents may cause a manufacturing procedure to be uneconomical. Harsh conditions and exotic reagents may also result in waste streams for the process which are difficult to handle or recycle, or have other disposal problems. Examples of such methods include treating fluoral, or a corresponding trifluoromethyl ketone, with either a Wittig or a Horner-Emmons reagent prepared from an α-halo ester (see Shen, Y. and Wang, T. J., *J. Chem. Res., Synop.*, 1993, 11,490; Ding, W., et. al., *J. Chem. Soc., Perkin Trans.*, 1993, 7, 855; Eguchi, T., et. al., *Tetrahedron Lett.*, 1992, 33, 5545). Mild reaction conditions have been used in those rare cases when an acidic hydrogen is in the α-position, such as using 1,1,1- trifluoro-3-nitro-2-propyl acetate to prepare the corresponding 1,1,1-trifluoro-3- nitropropene (see Iwata, S., et. al., *Bull. Chem. Soc. Jpn.*, 1993, 66, 2432).

I have discovered a method for preparing α,β-unsaturated esters of Formula I which does not require harsh conditions, expensive reagents, or the presence of a relatively acidic hydrogen in the a α-position in the starting material. Because of the surprisingly mild reaction conditions used, this method has the advantages both of ease of use and cost compared with known methods. In addition, the mild reaction conditions used generally result in higher yields of the desired product, higher purity, and fewer waste stream disposal problems.

DETAILED DESCRIPTION OF THE INVENTION

The present invention is a method for preparing α,β-unsaturated-β-trifluoromethyl carboxylates and related materials of Formula II

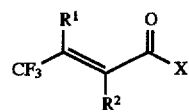

wherein X is selected from $OR^3$ and $NR^3R^4$, wherein each $R^1$, $R^2$, $R^3$, and $R^4$ is independently selected from hydrogen and unsubstituted or substituted $(C_1-C_6)$ alkyl, $(C_1-C_6)$ alkenyl, alkynyl, aryl, cycloalkyl, and heterocycle, wherein the substituents are independently selected from one to three of any base resistant functional group; comprising contacting a compound of Formula III

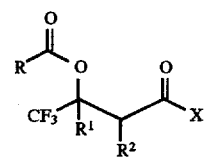

wherein R is selected from hydrogen and monovalent or polyvalent, unsubstituted or substituted $(C_1-C_{10})$ unbranched or branched alkyl, $(C_1-C_{10})$ unbranched or branched alkenyl, aryl, and heterocycle, wherein the substituents are independently selected from one to three of any base resistant functional group; with a base to produce the α,β-unsaturated compound of Formula II and a compound represented in the neutral form as Formula IV.

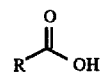

$R^1$, $R^2$, $R^3$ and $R^4$ are preferably selected from hydrogen; methyl; ethyl; isomers of propyl, butyl, pentyl, and hexyl; and phenyl. Hydrogen is the most preferred $R^1$ and $R^2$. Ethyl is the most preferred $R^3$ and $R^4$. Preferred R groups are the $(C_1-C_{10})$ alkyls; more preferred are $(C_1-C_4)$ alkyls; propyl is most preferred.

In a preferred embodiment, the α,β-unsaturated compound is an alkyl ester, that is, X is $OR^3$ wherein $R^3$ is alkyl, R is propyl, and $R^1$ and $R^2$ are hydrogen.

Another embodiment of this invention is a process for preparing an α,β-unsaturated-β-trifluoromethyl carboxylate of Formula II, comprising:

a. acylating a compound of Formula V:

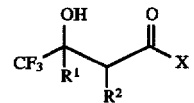

to produce an acylated compound, that is, a compound of Formula III wherein R is as defined above; and b. contacting the acylated compound with a base to produce the α,β-unsaturated compound and the acid corresponding to the compound of Formula IV.

The term "base resistant functional group" means a functional group which does not react with the base under the process conditions used in a manner which would adversely affect the production of the α,β-unsaturated compound. Preferred groups include $R^1$, OH, $OR^1$, $NR^1R^2$, $NO_2$, perhaloalkyl, and heterocycle, wherein $R^1$ and $R^2$ are as defined above. The term "heterocycle" means a 5- or 6-membered heterocycle containing from 1 to 3 heteroatoms selected from oxygen, sulfur, and nitrogen. The heterocycle may be an aromatic or a non-aromatic heterocycle including, for example, furyl, thienyl, aziridyl, pyridyl, oxazolyl, triazolyl, pyrazinly, pyrolyl, imidazolidinlyl, and piperidyl. The terms "monovalent" and "polyvalent" refer to the number of potential ester linkages that the moiety may form. Examples of monovalent groups include acetate and butyrate; examples of polyvalent groups include succinates and trimellitic esters.

When an acylating agent is used it should be chosen both for its ability to react with the compound of Formula V and for the chemical/physical properties of the resulting compound of Formula IV formed when the α,β-unsaturated compound is produced. Common inexpensive acylating agents such as acetic anhydride, acetyl chloride, butyric anhydride, and propionic anhydride are preferred. Most preferred are acetic and butyric anhydrides.

The process may be carried out in the presence or absence of a solvent. Solvent composition is not critical. However, the solvent should not react with the starting material, the base, or itself under the reaction conditions. The solvent can also be utilized as the base, when it contains a basic functional group. When a solvent is used, preferred solvents include ethers, alkanes, cycloalkanes, aromatic compounds, and pyridines and other aromatic nitrogen containing compounds. Most preferred solvents are selected from the alkanes and alkenes. The choice of a particular solvent will depend on the isolation procedure used and the physical/chemical properties of the solvent itself. It is most preferred to conduct the process in the absence of a solvent.

Likewise, the temperature in which the reaction is conducted is not critical. Key factors in choosing the reaction temperature include the boiling points of the reactants, products, and solvent, the type of separation process desired, and the thermal stability of the reactants, products, and solvent. One approach to determine the optimum temperature is to combine the reactants and, when used, the solvent at ambient temperature and then gradually increase the temperature until reaction occurs. In many cases, the α,β-unsaturated compound and/or the compound of Formula IV will have a boiling point below the reaction temperature. In such cases, distillation is a convenient and economical process to separate the reaction products from other components such as the solvent, the base, and impurities.

The base can be either an inorganic or an organic base. The base should preferably have a pKa greater than that of the α,β-unsaturated compound and the compound of Formula IV formed when the α,β-double bond is created. Preferred bases include the carbonates, bicarbonates and hydroxides of sodium, potassium, cesium, and lithium; substituted or unsubstituted pyridines; 1,8-diazabicyclo[5.4.0]undec-7-ene (commonly referred to as DBU); 1,5-diazabicyclo[4.3.0]non-5-ene (commonly referred to as DBN); and other amine containing bases with boiling points greater than the maximum temperature used in the process. Most preferred are the carbonates and hydroxides because of their low cost. In addition to discovering that relatively mild bases can be used in this process, we have also discovered that they can be used in a catalytic amount, that is, in an amount less than a stoichiometric amount. Use of such a catalytic amount of base not only reduces the cost of running the process but also reduces the number and quantities of side products and of impurities produced. This, in turn, reduces waste stream, recycle, and recovery problems.

In each of the above cases the base and the compound of Formula IV typically form a salt which is usually, but not always, separated from the solvent and the α,β-unsaturated compound. Such a separation step may include a neutralization step wherein the pH of the unseparated mixture is adjusted in order to place the components in an easily separable form. That is, in a neutral, acid, base, or salt form. The separation step may also include one or more distillation, filtration, centrifugation, solvent/solvent extraction, or water/solvent extraction steps.

The separation step may be a single process or a combination of two or more different processes, depending on the conditions chosen. By careful selection of the base, solvent (if a solvent is used), the R group, and the α,β-unsaturated compound formed, the type of separation used can be selected for manufacturing convenience. For example, when the compound of Formula IV is low boiling, the solvent is low boiling and water insoluble, and the base is water soluble, then the separation step can include the steps of water extraction of the base followed by distillation to remove the solvent and the compound of Formula IV. If the chosen solvent has a boiling point higher than the α,β-unsaturated compound formed then the α,β-unsaturated compound can be distilled from the solvent. In other cases it may be desirable to chose a solvent which is used in a later process step so that it is not necessary to separate the α,β-unsaturated compound from the solvent.

The following examples describe in detail some of the embodiments of this invention.

EXAMPLE 1

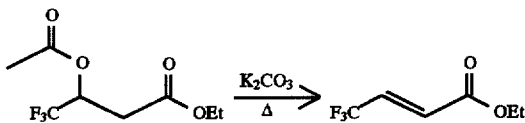

To a 50 mL round bottom flask equipped with a magnetic stir bar, oil bath, and a vacuum jacketed distilling apparatus with a 15 mm vigreux column, was added ethyl 3-acetyloxy-4,4,4-trifluorobutanoate (11.50 g, 50.4 mmol), and 0.50 g anhydrous potassium carbonate (3.6 mmol). The temperature of the oil bath was gradually raised to 140° C. at which time a reaction was noted. The oil bath temperature was gradually increased to 180° C. during which time 9.61 g of a clear distillate was collected.

Analysis of this material by $^1$H NMR showed it to be a 60:40 molar mixture of ethyl (E)-4,4,4-trifluorobut-2-enoate and acetic acid, 90% yield of the theoretical amount of ethyl (E)-4,4,4-trifluorobut-2-enoate.

EXAMPLE 2

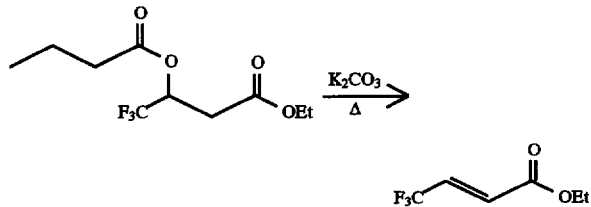

In the same manner described in example 1, ethyl 3-(1-oxobutoxy)-4,4,4-trifluoro-butanoate (15.00 g, 58.5 mmol) was reacted with 0.50 g of potassium carbonate (3.6 mmol). As the oil bath temperature was gradually raised from 160°–200° C., 10.78 g of distillate was collected.

This material was found by 1H NMR to be 86 mole% ethyl (E)-4,4,4-trifluorobut-2-enoate and 14 mole% butyric acid (100% of the theoretical amount of ethyl (E)-4,4,4-trifluorobut-2-enoate. The residue in the pot (4.31 g) was found to be mostly butyric acid.

EXAMPLE 3

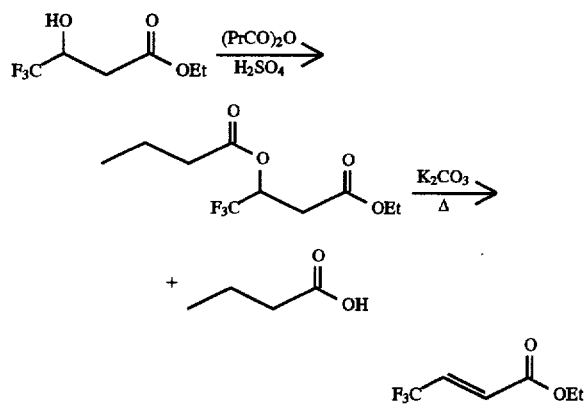

To a 100 ml 3-neck round bottom flask equipped with a magnetic stir bar, thermometer/Therm-O-Watch assembly, and a pressure equalizing addition funnel was added ethyl 3-hydroxy-4,4,4-trifluorobutanoate (40.00 g, 214.9 mmol), and 1 drop of concentrated sulfuric acid. Via the addition funnel butyric anhydride (35.70 g, 225.7 mmol) was added dropwise over a 15 minute period. A peak reaction temperature of 66° C. was observed.

After approximately 30 minutes, the addition funnel was replaced with a vacuum jacketed distilling apparatus with a 15 mm vigreux column. Anhydrous potassium carbonate (3.00 g,21.7 mmol) was added and the resulting mixture was gently heated. At approximately 145° C. (pot temperature) a distillate began to form. Over a 1 h period, the pot temperature was raised from 145°–160° C. during which time 33.77 g of clear distillate was collected.

Analysis of this material by 1H NMR showed it to be 93 wt% ethyl (E)-4,4,4-trifluorobut-2-enoate (87% yield) and 7 wt % butyric acid.

EXAMPLE 4

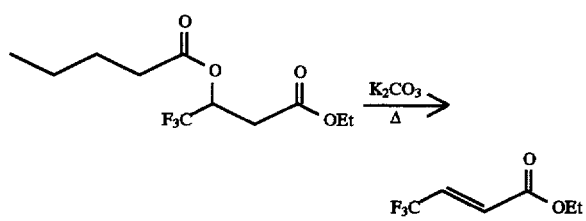

To a 50 mL 3-neck round bottom flask equipped with a magnetic stir bar, thermometer/.Therm-O-Watch assembly, and a vacuum jacketed distilling apparatus with a 15 mm vigreux column, was added 2-ethoxycarbonyl-1-(trifluoromethyl)ethyl pentanoate (29.00 g, 99.9 mmol), and potassium carbonate (1.10 g, 8.0 mmol). The stirred reaction mixture was gradually heated. As the pot temperature was gradually raised from 140° C. (onset of reaction) to 165° C. over a 1 h period, 16.07 g (89%) of ethyl (E)-4,4,4-trifluorobut-2-enoate was collected.

EXAMPLE 5

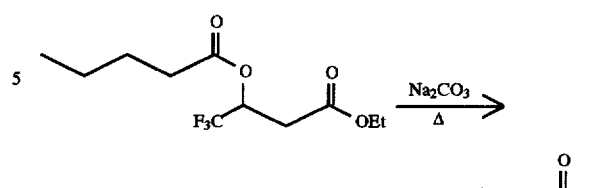

To a 50 mL 3-neck round bottom flask equipped as described in example 4 was added 2-ethoxycarbonyl-1-(trifluoromethyl)ethyl pentanoate (28.21 g, 104.4 mmol), and sodium carbonate (1.00 g, 9.4 mmol). The stirred mixture was heated to 140° C. at which point the sodium carbonate began to react and a distillate began to form. With continued heating, a distillate was collected as the pot temperature was slowly raised to 175° C. over approximately a 1 h period. This afforded 15.90 g (91%) of ethyl (E)-4,4,4-tri-fluorobut-2-enoate.

EXAMPLE 6

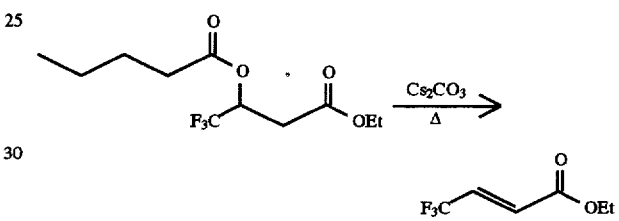

To a 50 mL 3-neck round bottom flask equipped as described in example 4 was added 2-ethoxycarbonyl-1-(trifluoromethyl)ethyl pentanoate (24.87 g, 92.0 mmol), and cesium carbonate (2.00 g, 9.4 mmol). The stirred mixture was heated to 80° C. at which point the cesium carbonate began to react. With continued heating, a distillate was collected as the pot temperature was slowly raised to 170° C. over approximately a 1 h period. This afforded 13.47 g (87%) of ethyl (E)-4,4,4-tri-fluorobut-2-enoate.

EXAMPLE 7

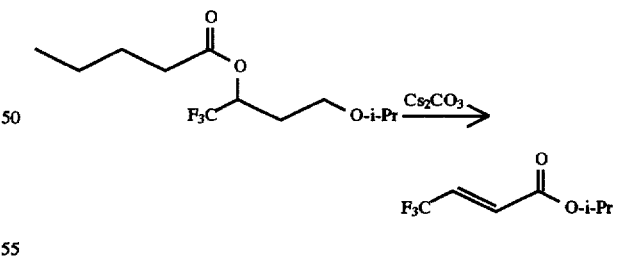

To a 50 mL 3-neck round bottom flask equipped as described in example 4 was added 29.50 g of a 95:5 mixture of 2-(2-propoxycarbonyl)-1-(trifluoromethyl)ethyl pentanoate and 2-ethoxycarbonyl-1-(trifluoromethyl)ethyl pentanoate, and 3.00 g of cesium carbonate. The stirred mixture was heated to 105° C. at which point the cesium carbonate began to react. With continued heating, 17.23 g of distillate was collected as the pot temperature was slowly raised to 180° C. over a 1 h period. The crude product was redistilled at 110°–112° C. to afford 16.31 g of a 95:5 mixture of isopropyl (E)-4,4,4-tri-fluorobut-2-enoate and ethyl (E)-4,4,4-trifluorobut-2-enoate.

EXAMPLE 8

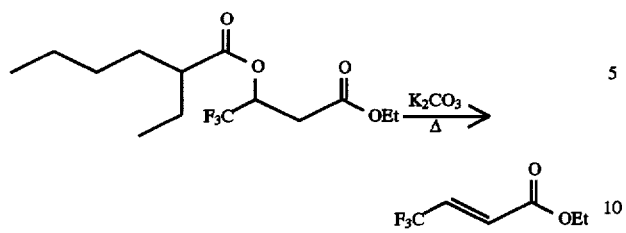

To a 100 ml 3-neck round bottom flask equipped as described in example 4 was added 2-ethoxycarbonyl-1-(trifluoromethyl)ethyl 2-ethylhexanoate (37.50 g, 120.0 mmol), and 1.50 g of anhydrous potassium carbonate (10.9 mmol). The stirred mixture was heated to 140° C. at which time the potassium carbonate reacted, and a distillate began to form. The pot temperature was slowly raised to 175° C. over a 1 h period during which time 17.20 g (85%) of ethyl (E)-4,4,4-trifluorobut-2-enoate was collected.

EXAMPLE 9

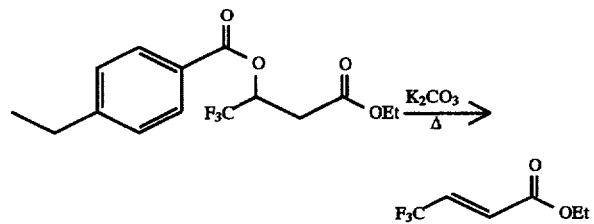

To a 100 mL 3-neck round bottom flask equipped as described in example 4 was added 2-ethoxycarbonyl-1-(trifluoromethyl)ethyl 4-ethylbenzoate (37.25 g, 117.0 mmol), and 1.50 g of anhydrous potassium carbonate (10.9 mmol). The stirred mixture was heated to 150° C. at which time the potassium carbonate reacted, and a distillate began to form. The pot temperature was slowly raised to 175° C. over a 1 h period during which time 14.67 g (75%) of ethyl (E)-4,4,4-trifluorobut-2-enoate was collected.

EXAMPLE 10

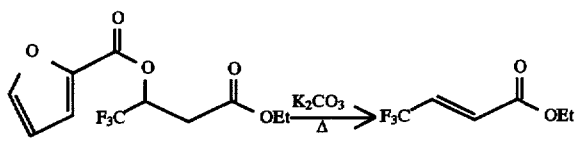

To a 50 mL 3-neck round bottom flask equipped as described in example 4 was added 2-ethoxycarbonyl-1-(trifluoromethyl)ethyl 2-furanoate (32.15 g, 114.7 mmol), and 1.20 g of potassium carbonate (8.7 mmol). The stirred mixture was heated to 160° C. at which time the potassium carbonate reacted, and a distillate began to form. The pot temperature was slowly raised to 180° C. over a 1 h period during which time 18.09 g (92%) of ethyl (E)-4,4,4-trifluorobut-2-enoate was collected.

EXAMPLE 11

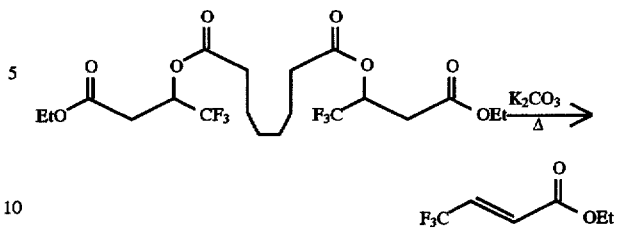

To a 500 mL 3-neck round bottom flask equipped with an air driven overhead stir motor, thermometer, and pressure equalizing addition funnel was added ethyl 3-hydroxy-4,4,4-trifluorobutanoate (25.00 g, 134.3 mmol), 4-(dimethylamino)pyridine (0.50 g, 4.1 mmol), triethylamine (21.0 mL, 150.7 mmol), and 200 mL of anhydrous diethyl ether. The addition funnel was charged with suberoyl chloride (14.18 g, 67.17 mmol), and 10 mL of anhydrous diethyl ether. With the aid of art ice/salt cooling bath, the suberoyl chloride was added dropwise over a 15 minute period while maintaining a reaction temperature at, or below, 10° C. At the end of the addition the ice bath was removed and the resulting slurry was allowed to stir for 1 h. To the stirring mixture was added 100 mL each of water and hexanes. After a few minutes, stirring was stopped and the mixture transferred to a separatory funnel. The lower aqueous phase was discarded. The organic phase was washed twice with 2N hydrochloric acid, once with water, twice with saturated NaHCO₃ solution, and once with brine. The solution was dried (MgSO₄) and concentrated using a rotory evaporator to yield a yellow liquid. Residual solvent was removed under vacuum to afford 33.15 g (97%) of di(2-ethoxycarbonyl-1-(trifluoromethyl)ethyl) octane-1,8-dioate as a yellow liquid.

To a 50 mL 3-neck round bottom flask equipped as described in example 4 was added 32.12 g (62.9 mmol) of the tetra ester described above, and 1.20 g (8.7 mmol) of anhydrous potassium carbonate. The stirred mixture was heated to 125° C. at which time the potassium carbonate reacted. With continued heating, distillate was collected as the pot temperature was gradually raised from 135°–180° C. over a 1 h period. This afforded 17.52 g (83%) of ethyl (E)-4,4,4-trifluorobut-2-enoate.

EXAMPLE 12

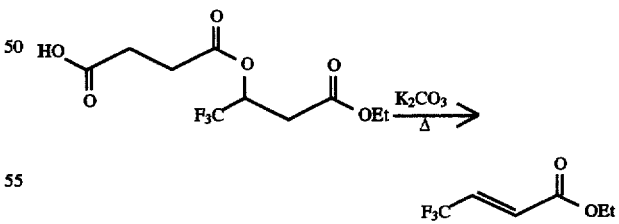

To a 500 mL round bottom flask equipped with a magnetic stir bar, and reflux condenser was added ethyl 3-hydroxy-4,4,4-trifluorobutanoate (25.00 g, 134.3 mmol), succinic anhydride (14.80 g, 148.0 mmol), 4-(dimethylamino)pyridine (0.50 g, 4.1 mmol), tri-ethylamine (21.0 mL, 150.7 mmol), and 200 mL of tert-butyl methyl ether. The resulting mixture was heated and allowed to reflux for 23 h. After cooling to ambient temperature, the mixture was transferred to a separatory funnel and washed twice with 2N hydrochloric acid. The organic phase was washed with water, saturated brine solution, dried (MgSO$_4$), and concentrated to a clear brown liquid using a rotory evaporator. Residual solvent was removed under vacuum and a small amount of succinic acid precipitated from the liquid. The crude product was diluted with a small amount of toluene and filtered to remove the succinic acid. Toluene was removed under reduced pressure to yield 29.12 g of a light brown oil.

To a 50 mL 3-neck round bottom flask equipped as described in example 4 was added 28.45 g of the product described above, and 1.00 g (7.2 mmol) of potassium carbonate. The stirred mixture was heated to 80° C. at which time the potassium carbonate reacted. With continued heating, a distillate was collected as the pot temperature was slowly raised to 185° C. over a 1 h period. The distillate was found to contain a few drops of water which was removed by pipet from the product. This afforded 14.00 g of ethyl (E)-4,4,4-trifluorobut-2-enoate.

EXAMPLE 13

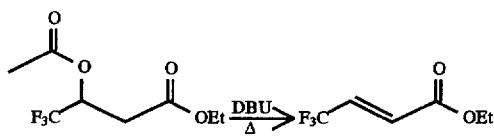

To a 50 mL 3-neck round bottom flask equipped as described in example 4 was added ethyl 3-acetyloxy-4,4,4-trifluorobutanoate (23.11 g, 101.3 mmol), and 2.00 g of 1,8-diaza-bicyclo[5.4.0]undec-7-ene (13.1 mmol). The stirred mixture was heated to 120° C. at which time a distillate began to collect. After most of the distillate had been collected, about 1 h, the pot temperature was briefly raised to 140° C. at which point the distillation was stopped. This afforded 17.81 g of a clear pungent liquid found to contain 70 mole% (E)-4,4,4-trifluorobut-2-enoate and 30 mole% acetic acid (NMR analysis).

EXAMPLE 14

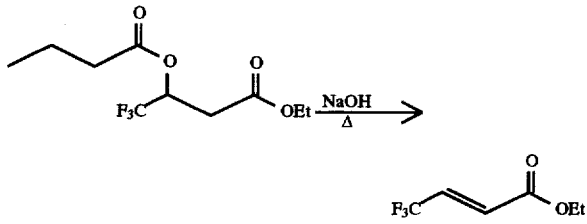

To a 50 mL 3-neck round bottom flask equipped as described in example 4 was added ethyl 3-(1-oxobutoxy)-4,4,4-trifluorobutanoate (26.13 g, 102.0 mmol), and 0.49 g of sodium hydroxide pellets (12.2 mmol). The mixture was heated to approximately 140° C. at which time the sodium hydroxide began to react and a distillate started to collect. With continued heating, a distillate was collected as the pot temperature was slowly raised to 160° C. over a 1 h period. The distillate was found to contain a few drops of water which as removed by pipet. This afforded 13.90 g of product found to be 99% E)-4,4,4-trifluorobut-2-enoate and 1% butyric acid (GC analysis).

EXAMPLE 15

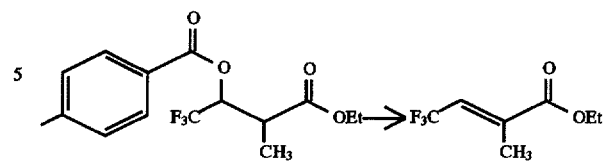

To a 50 mL round bottom flask equipped with a magnetic stir bar, oil bath, and a vacuum jacketed distilling apparatus with a 15 cm Vigreuex column was added ethyl 2-methyl-3-p-toluoyloxy-4,4,4-trifluorobutanoate (28.00 g, 88 mmol), and 1.75 g of bicyclo[5.4.0]un-dec-7-ene (DBU). The stirred mixture was heated by raising the oil bath temperature gradually to 170° C. A distillate was collected boiling between 125°–133° C. The temperature of the bath was raised to 180° C. briefly before being allowed to cool to room temperature. A total of 12.23 g (76%) of distillate was collected. This material was analyzed by gas chromatography, $^1$H and $^{13}$C NMR spectroscopy, and was found to be identical to an authentic sample of ethyl 2-methyl-4,4,4-trifluorobutanoate.

I claim:
1. A method for preparing an α,β-unsaturated-β-trifluoromethyl carboxylate of the formula:

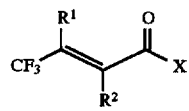

wherein X is selected from OR$^3$ and NR$^3$R$^4$ and wherein each R$^1$, R$^2$, R$^3$, and R$^4$ is independently selected from hydrogen and unsubstituted or substituted (C$_1$–C$_6$) alkyl, (C$_1$–C$_6$) alkenyl, alkynyl, aryl, cycloalkyl, heterocycle, wherein the substituents are independently selected from one to three of any base resistant functional group;

comprising contacting a compound of the formula:

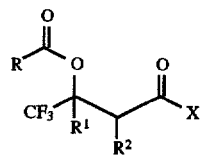

wherein R is selected from hydrogen and monovalent or polyvalent, unsubstituted or substituted (C$_1$–C$_{10}$) unbranched or branched alkyl, (C$_1$–C$_{10}$) unbranched or branched alkenyl, aryl, and heterocycle, wherein the substituents are independently selected from one to three of any base resistant functional group;

with a base to produce the α,β-unsaturated compound and a compound represented in the neutral form as a carboxylic acid of the formula:

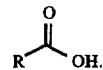

2. The method of claim 1 further comprising the step of separating the α,β-unsaturated compound from the base and the acid.

3. The method of claim 1 wherein each R$^1$, R$^2$, R$^3$, and R$^4$ is independently selected from hydrogen; methyl; ethyl; isomers of propyl, butyl, pentyl, and hexyl; and phenyl.

4. The method of claim 1 wherein R is a branched or unbranched ($C_1$–$C_{10}$) alkyl.

5. The method of claim 1 wherein the base is selected from the carbonates, bicarbonates and hydroxides of sodium, potassium, cesium, and lithium; substituted or unsubstituted pyridine; 1,8-diazabicyclo[5.4.0]undec-7-ene; and 1,5-diazabicyclo[4.3.0]non-5-ene.

6. The method of claim 1 wherein the base is potassium carbonate.

7. The method of claim 1 wherein the base is used in a catalytic amount.

8. The method of claim 1 wherein $R^1$ and $R^2$ are hydrogen.

9. The method of claim 1 wherein $R^3$ and $R^4$ are ethyl.

10. The method of claim 1 wherein R is propyl.

11. A method for preparing an α,β-unsaturated-β-trifluoromethyl carboxylate of the formula:

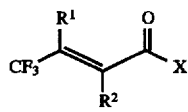

comprising:

a. acylating a compound of the formula:

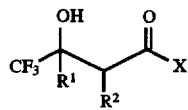

wherein X is selected from $OR^3$ and $NR^3R^4$ and wherein each $R^1$, $R^2$, $R^3$, and $R^4$ is independently selected from hydrogen and unsubstituted or substituted ($C_1$–$C_6$) alkyl, ($C_1$–$C_6$) alkenyl, alkynyl, aryl, cycloalkyl, heterocycle, wherein the substituents are independently selected from one to three of any base resistant functional group;

to produce an acylated compound of the formula:

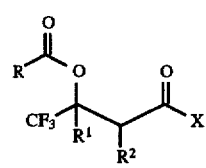

wherein R is selected from hydrogen and monovalent or polyvalent, unsubstituted or substituted, unbranched or branched ($C_1$–$C_6$) alkyl, unbranched or branched ($C_1$–$C_6$) alkenyl, aryl, and heterocycle, wherein the substituents are independently selected from one to three of any base resistant functional group;

b. contacting the acylated compound with a base to produce the α,β-unsaturated compound and an acid of the formula

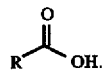

12. The method of claim 11 further comprising the step of separating the α,β-unsaturated compound from the base and the acid.

13. The method of claim 11 wherein each $R^1$, $R^2$, $R^3$, and $R^4$ is independently selected from hydrogen; methyl; ethyl; isomers of propyl, butyl, pentyl, and hexyl; and phenyl.

14. The method of claim 11 wherein the acylating agent is selected from acetic anhydride, acetyl chloride, butyric anhydride, and propionic anhydride.

15. The method of claim 11 wherein $R^1$ and $R^2$ are hydrogen.

16. The method of claim 11 wherein $R^3$ and $R^4$ are ethyl.

17. The method of claim 11 wherein R is propyl.

* * * * *